United States Patent
Lee et al.

(10) Patent No.: US 7,690,380 B2
(45) Date of Patent: *Apr. 6, 2010

(54) SURGICAL DRAPE HAVING A FLUID COLLECTION POUCH WITH AN INFLATABLE RIM

(75) Inventors: Dan R. Lee, Columbus, MS (US);
Michael A. Gil, West Point, MS (US);
Lewis Dorsey Cox, Leeds, AL (US);
Lloyd G. B. Cooper, Birmingham, AL (US)

(73) Assignee: Ecolab Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/467,800

(22) Filed: Aug. 28, 2006

(65) Prior Publication Data

US 2007/0017529 A1    Jan. 25, 2007

Related U.S. Application Data

(63) Continuation of application No. 10/655,495, filed on Sep. 4, 2003, now Pat. No. 7,096,871, which is a continuation-in-part of application No. 10/235,309, filed on Sep. 5, 2002, now abandoned.

(51) Int. Cl.
*A61B 19/08* (2006.01)
(52) U.S. Cl. .................. 128/853; 128/849; 604/327
(58) Field of Classification Search ............. 128/847, 128/851–854, 855, 849; 5/713; 604/322, 604/327, 328, 332
See application file for complete search history.

(56) References Cited

U.S. PATENT DOCUMENTS 542,202 A    7/1895    Morrison (Continued)

FOREIGN PATENT DOCUMENTS

WO    WO 97/09001    3/1997

(Continued)

OTHER PUBLICATIONS

Notification of Transmittal of the International Search Report for PCT Application No. PCT/US03/27927 filed May 9, 2003, authorized by Johannes Van Brummelen, 7 pages, Jan. 23, 2004.

(Continued)

*Primary Examiner*—Patricia M Bianco
*Assistant Examiner*—Camtu T Nguyen
(74) *Attorney, Agent, or Firm*—Andrew D. Sorensen; Laura C. Dilorenzo

(57) ABSTRACT

According to one embodiment of the invention, an apparatus used for collecting fluids during a medical procedure includes a fluid collection pouch having an open end, an inflatable bladder substantially surrounding a perimeter of the open end, and a pump coupled to the inflatable bladder. The pump is operable to inflate the inflatable bladder. According to another embodiment of the invention, an apparatus used for collecting fluids during a medical procedure includes a fluid collection pouch having an open end with a perimeter, a channel surrounding approximately one half of the perimeter of the open end, an inflatable bladder disposed within the channel, and a pump disposed within the channel and coupled to the inflatable bladder. The pump is operable to inflate the inflatable bladder.

31 Claims, 4 Drawing Sheets

U.S. PATENT DOCUMENTS

| | | | |
|---|---|---|---|
| 759,084 A | 5/1904 | Eggers et al. | |
| 762,737 A | 6/1904 | Meinecke et al. | |
| 763,304 A | 6/1904 | Meinecke et al. | |
| 1,741,836 A | 12/1929 | Gilbert | |
| 1,864,434 A | 6/1932 | Hart | |
| 2,658,512 A | 11/1953 | Tcheong | |
| 3,418,663 A | 12/1968 | Scott | |
| 3,816,858 A | 6/1974 | Martin | |
| 4,974,604 A * | 12/1990 | Morris | 128/853 |
| 5,002,069 A | 3/1991 | Thompson et al. | |
| 5,144,708 A | 9/1992 | Pekar | |
| 5,342,385 A | 8/1994 | Norelli et al. | |
| 5,372,487 A | 12/1994 | Pekar | |
| 5,419,343 A | 5/1995 | Taylor | |
| 5,514,081 A | 5/1996 | Mann | |
| 5,558,654 A | 9/1996 | Hardy | |
| 5,709,221 A | 1/1998 | Vancaillie et al. | |
| 6,070,586 A | 6/2000 | Harroll et al. | |
| 6,314,958 B1 | 11/2001 | Harroll et al. | |
| 6,442,962 B1 | 9/2002 | Gaetke et al. | |
| 6,782,640 B2 | 8/2004 | Westin | |

OTHER PUBLICATIONS

"Specialty Orthopedic Products, Innovation by Design . . . ™ Featuring Equipment Drapes and Patient Drapes," © 1994 *Microtek Medical*, inc., 1994.

"Innovation by Design, OB/Gyn Pouch Drapes, Under buttocks pouch drapes that effectively collect surgical fluids during any procedures . . . Obstetrics, Gynecology, Urology" © 1994 *Microtek Medical*, inc., 1994.

Canadian Intellectual Property Office Report, Application No. 2,497,341, 3 pages, Apr. 9, 2009.

* cited by examiner

SURGICAL DRAPE HAVING A FLUID COLLECTION POUCH WITH AN INFLATABLE RIM

RELATED APPLICATIONS

This application is a continuation of U.S. application Ser. No. 10/655,495, filed Sep. 4, 2003 entitled "SURGICAL DRAPE HAVING A FLUID COLLECTION POUCH WITH AN INFLATABLE RIM," now U.S. Pat. No. 7,096,871.

U.S. application Ser. No. 10/655,495 is a continuation-in-part of U.S. application Ser. No. 10/235,309 filed Sep. 5, 2002, entitled "SURGICAL DRAPE HAVING A FLUID COLLECTION POUCH WITH AN INFLATABLE RIM," now abandoned.

TECHNICAL FIELD OF THE INVENTION

The present invention relates generally to the field of surgical drapes, and more particularly to a surgical drape having a fluid collection pouch with an inflatable rim.

BACKGROUND OF THE INVENTION

Numerous surgeries and other medical procedures are performed in hospitals and medical buildings everyday across the world. Depending on the type of surgery being performed, there is usually surgical and/or bodily fluids that are encountered during the procedure. Medical personnel use collection pouches to collect these fluids to prevent spillage of the fluids, to keep the fluids away from the patient, and to protect operating room personnel. Medical personnel, therefore, desire that these collection pouches be easy to use and perform their function in a reliable manner.

Some previous collection pouches have malleable wires around a perimeter of their open end that allow medical personnel to shape the perimeter of the collection pouch in a desired configuration. However, once the malleable wire is shaped in a certain way, it stays that way or collapses under pressure. Collection pouches having these malleable wires may be inadequate to conform adequately to a portion of a patient's body or to fully support the pouch when open. In addition, when a surgeon is finished with a particular positioning of the surgical tool, then one portion of the perimeter of the open end may be in such a position that surgical and/or bodily fluids leak out of the collection pouch and onto the floor, which is undesirable.

Some previous collection pouches have a foam material around a perimeter of their open end that offered some stiffness to the perimeter so that the pouch could stay open, yet be resilient enough to allow a surgeon to position his or her hand or a surgical tool without much resistance from the foam material. However, these foam-rimmed pouches were unreliable. Because of the environment the pouch is used in, the foam material has a tendency to crackle and peel to the extent that some of the foam material may fall into the surgical area, which is undesirable. To address this problem, the foam material was encased within a housing. However, these types of pouches had packaging and shipping problems, as well as additional manufacturing expense.

SUMMARY OF THE INVENTION

According to one embodiment of the invention, an apparatus used for collecting fluids during a medical procedure includes a fluid collection pouch having an open end, an inflatable bladder substantially surrounding a perimeter of the open end, and a pump coupled to the inflatable bladder. The pump is operable to inflate the inflatable bladder.

According to another embodiment of the invention, an apparatus used for collecting fluids during a medical procedure includes a fluid collection pouch having an open end with a perimeter, a channel surrounding approximately one half of the perimeter of the open end, an inflatable bladder disposed within the channel, and a pump disposed within the channel and coupled to the inflatable bladder. The pump is operable to inflate the inflatable bladder.

Embodiments of the invention provide a number of technical advantages. Embodiments of the invention may include all, some, or none of these advantages. One technical advantage is a surgical drape that has "shape memory." Surgeons or other medical personnel oftentimes have to deform the rim of the collection pouch to facilitate specific positioning of a surgical instrument. Having one or more inflatable bladders around a perimeter of a fluid collection pouch allows a surgeon or other medical personnel to deform the inflatable rim with the assurance the rim will reform to its original shape after the deforming. This helps to prevent spillage of surgical and/or other fluids from the surgical site in addition to saving the surgeon valuable time from not having to reshape the rim themselves. An inflatable rim also facilitates better conformability. The inflatable rim naturally follows the contours of a patients body parts, which may help to avoid any fluids from touching the patient or the bed that the patient is lying on. A surgical drape having an inflatable rim also may be packaged and shipped with the inflatable rim in a deflated state, which is easier and less expensive than shipping surgical drapes having foam rims.

Other technical advantages are readily apparent to one skilled in the art from the following figures, descriptions, and claims.

BRIEF DESCRIPTION OF THE DRAWINGS

For a more complete understanding of the invention, and for further features and advantages, reference is now made to the following description, taken in conjunction with the accompanying drawings, in which.

DETAILED DESCRIPTION OF EXAMPLE EMBODIMENTS OF THE INVENTION

Figure 1:
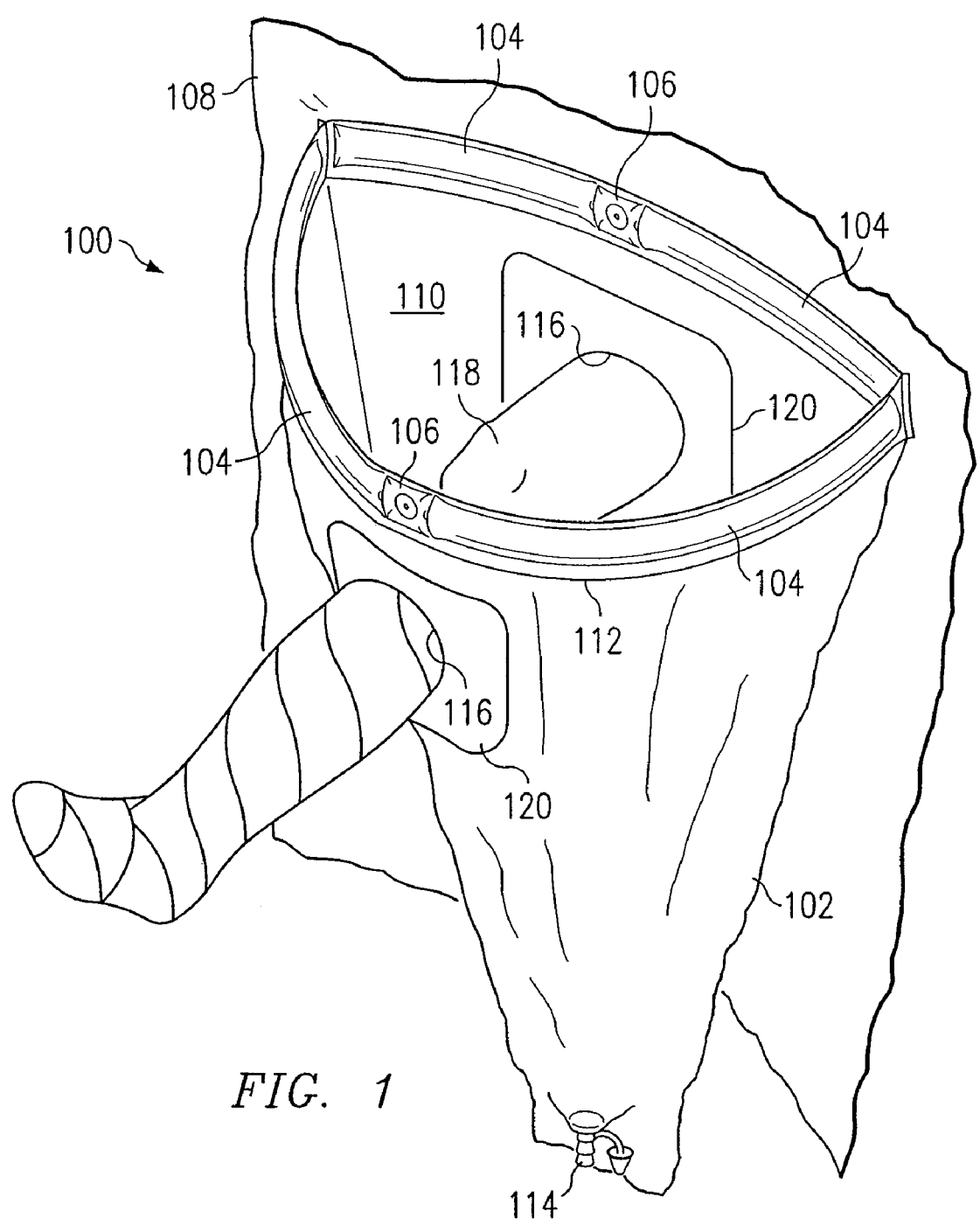
FIG. 1 is a perspective view of a surgical drape having a fluid collection pouch with an inflatable rim being used to collect fluids during a surgical procedure in accordance with one embodiment of the present invention.
Figure 2A:
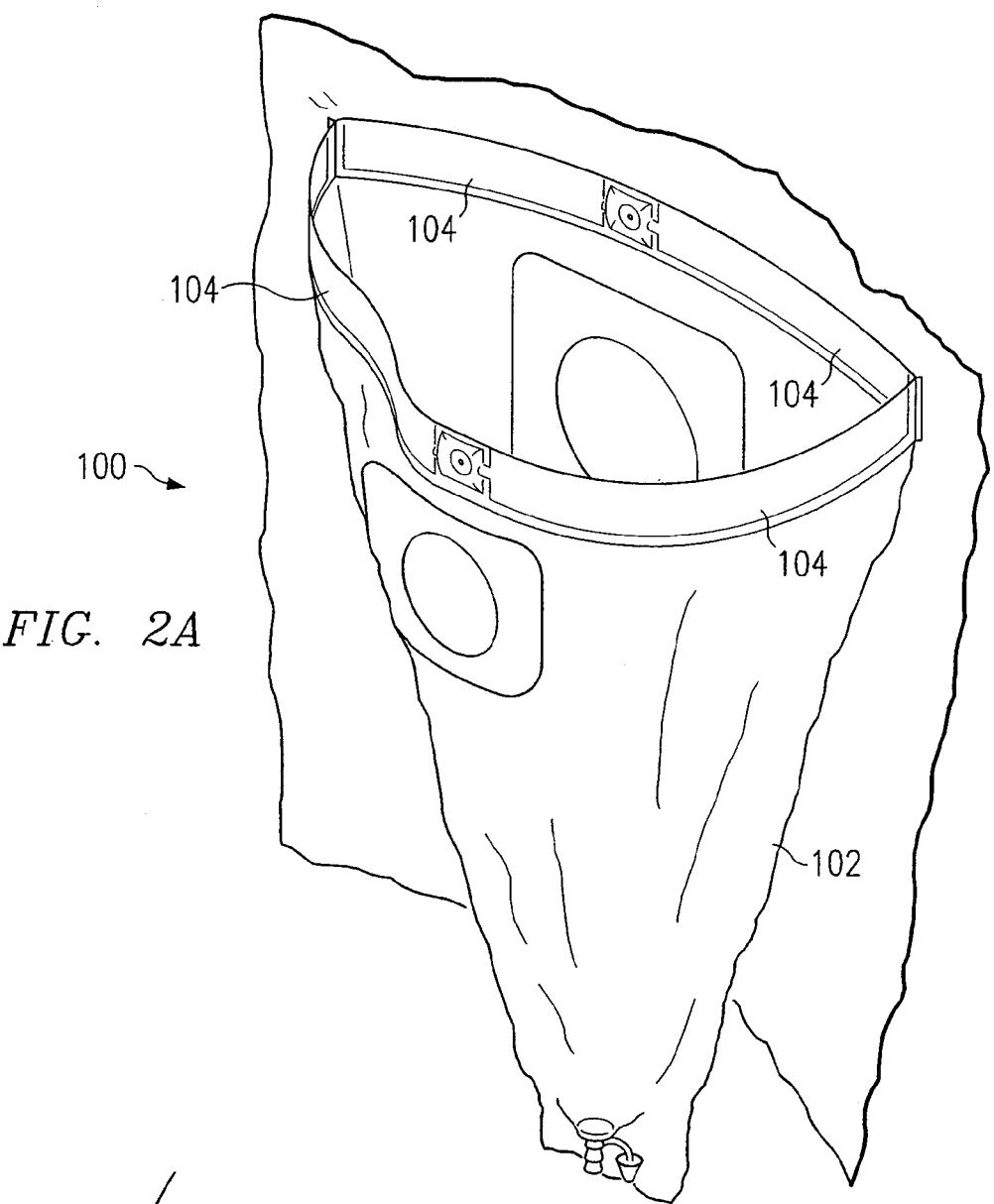
FIG. 2A is a perspective view of the inflatable rim of the collection pouch of FIG. 1 showing the inflatable rim in a deflated state.
Figure 2B:
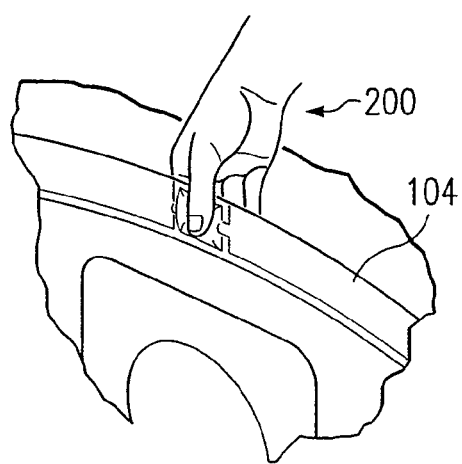
FIGS. 2B through 2E are perspective views of the inflatable rim of the collection pouch of FIG. 1 being inflated by a user in accordance with various embodiments of the present invention.
Figure 2C:
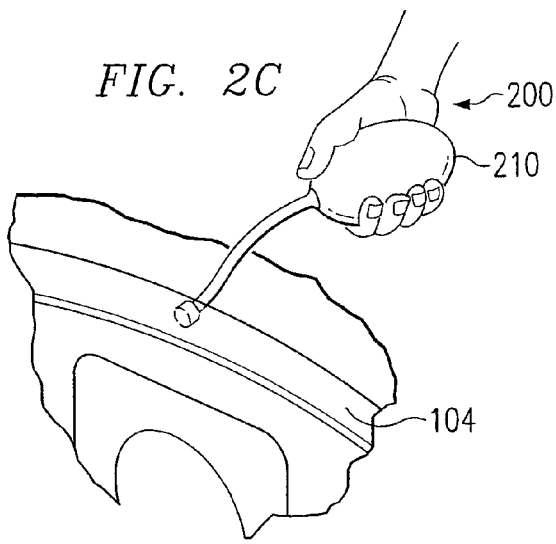
Figure 2D:
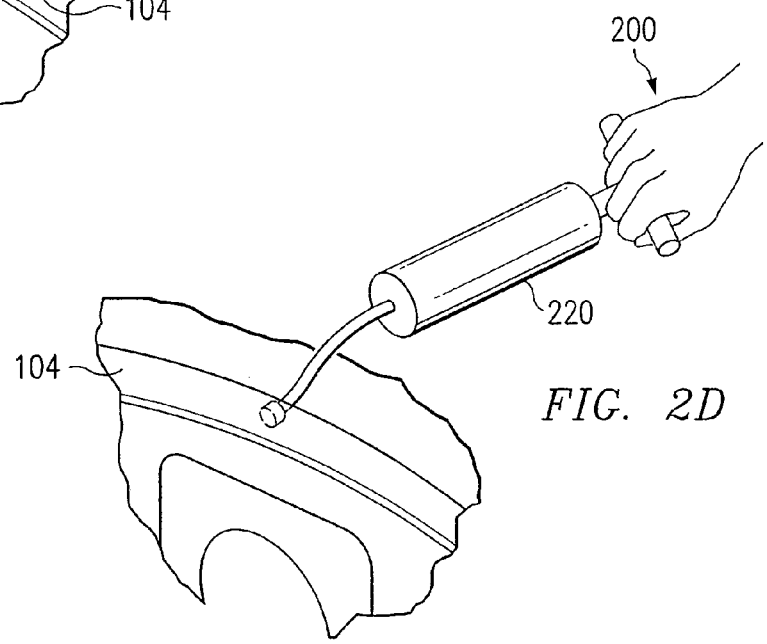
Figure 2E:
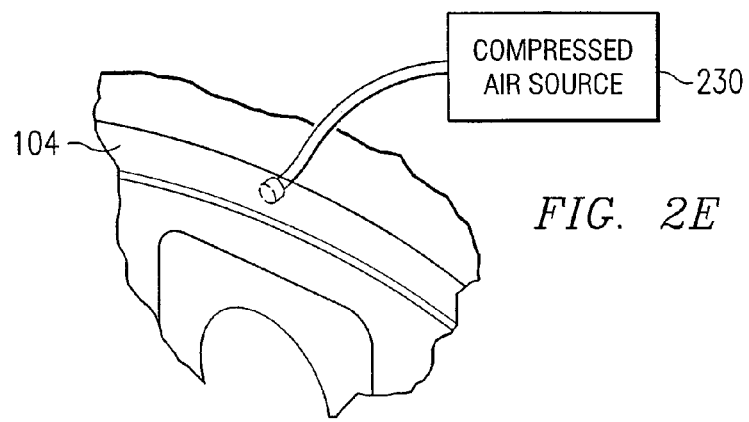
Figure 3:
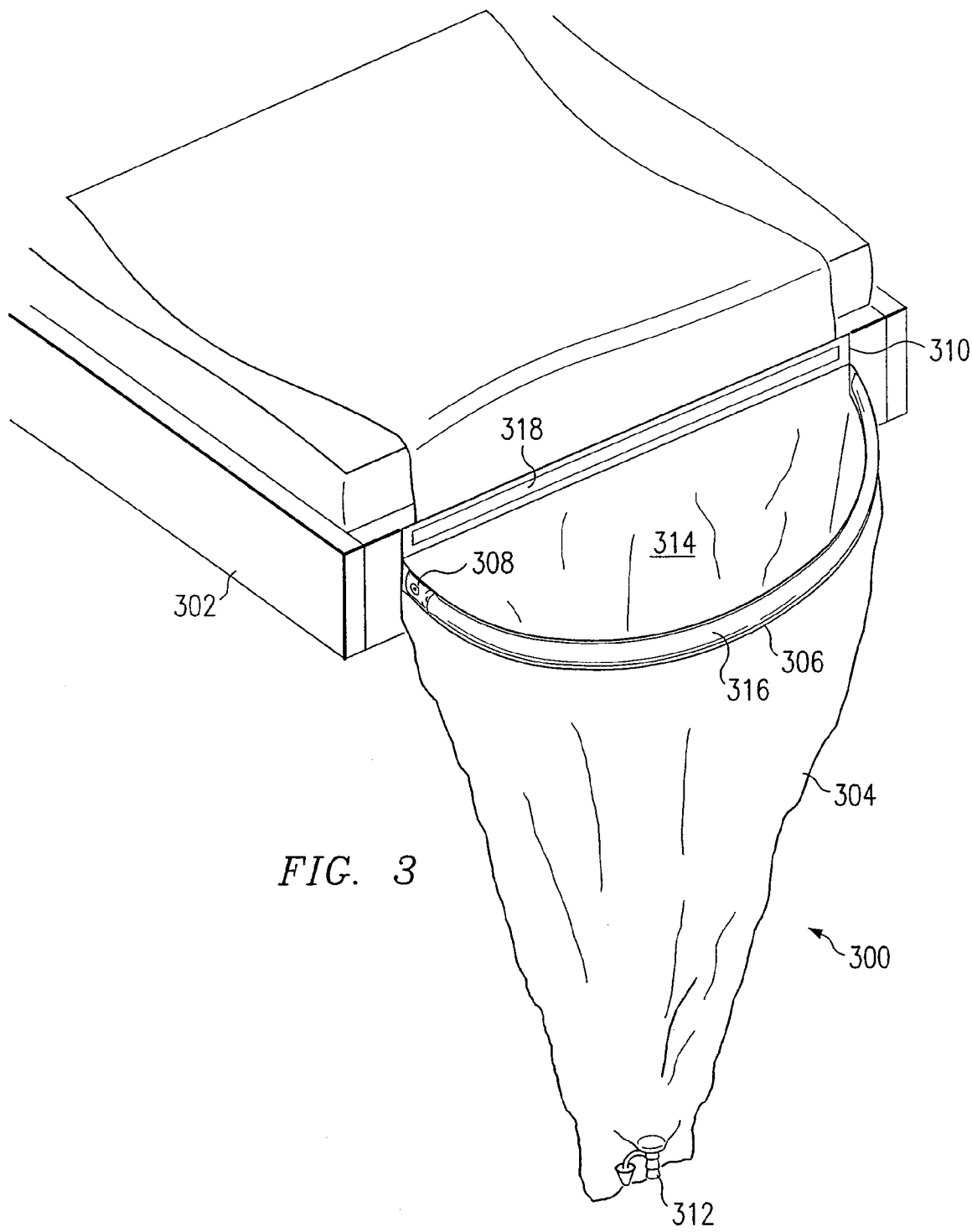
FIG. 3 is a perspective view of another surgical drape having a fluid collection pouch with an inflatable rim being used to collect fluids during a surgical procedure in accordance with another embodiment of the present invention.

Example embodiments of the present invention and their advantages are best understood by referring now to FIGS. 1-3 of the drawings, in which like numerals refer to like parts.

FIG. 1 is a perspective view of a surgical drape 100 being utilized during a surgical procedure according to one embodiment of the present invention. In the illustrated embodiment, surgical drape 100 is being utilized during knee surgery;

however, surgical drape 100 may be utilized during other surgical procedures or other medical procedures. The term surgery as used herein may mean any suitable medical procedures. Surgical drape 100 functions to collect surgical fluids, bodily fluids and/or tissue, and other suitable fluids or materials encountered during surgery. As illustrated in FIG. 1, surgical drape 100 includes a fluid collection pouch 102, a plurality of inflatable bladders 104, a pair of pumps 106, and a patient drape 108.

Fluid collection pouch 102 is illustrated in FIG. 1 to be a generally cone-shaped pouch formed from a low density polyethylene. However, fluid collection 102 may be any suitable shape and may be formed from any suitable fluid-impervious material. Fluid collection pouch 102 may also be formed from a transparent material, translucent material, or an opaque material. Fluid collection pouch includes an open end 110 that allows a surgeon, a doctor, or other suitable medical personnel to access the surgical area. A perimeter of open end 110 may include a channel 112 that houses inflatable bladder 104. To form channel 112, open end 110 of fluid collection pouch 102 may be curled and sealed back to itself or may be formed in other suitable manners. Channel 112 may alternatively be a separate element that is coupled to fluid collection pouch 102.

At the lower end of fluid collection pouch 102 is a drainage port 114 that facilitates the draining of any fluids collected during surgery. Drainage port 114 may facilitate the draining of the fluid by gravity or by the coupling of a suction device to drainage port 114. Drainage port 114 may be any suitable fitting that is coupled to fluid collection pouch 102 in any suitable manner.

Fluid collection pouch 102 also includes opposed apertures 116 formed in its wall. Apertures 116 are adapted to accept a limb 118 of a patient to facilitate surgery. Surrounding apertures 116 may be a flexible material 120 that conforms to the patient's limb 118 in a such a manner that it prevents surgical and/or bodily fluids from leaking between patient's limb 118 and apertures 116. Flexible material 120, which may be any suitable size and shape, may be formed from any suitable material, such as an elasticized polymer. In a particular embodiment, flexible material 120 is formed from Kraton™ manufactured by Shell Chemical Company.

Inflatable bladders 104 substantially surround the perimeter of open end 110 of fluid collection pouch 102. The function of inflatable bladders 104 is to allow a surgeon or other medical personnel to deform the perimeter of open end 110 with the assurance that it will reform to its original shape after deforming. For example, if a surgeon needs to position a surgical tool in a certain position for surgery, then a portion of the perimeter of open end 110 will be contorted because of the hand position of a surgeon or the position of a surgical tool adjacent the surgical area. When the surgical tool is removed or the surgeon steps away from the surgical area, inflatable bladders 104 reforms to its natural position as a result of the air pressure therein. This helps to prevent spillage of surgical and/or other fluids from the surgical area in addition to saving the surgeon or other medical personnel valuable time from not having to re-shape the perimeter of open end 110 as in previous surgical drapes that had malleable rims. The malleable rims also do not prevent spillage as well as inflatable bladders 104. Previous surgical drapes having foam material rims did fairly well to prevent spillage; however, the foam rims had a tendency to be brittle and to crackle, which sometimes led to pieces of the foam falling into the surgical area. The foam material may be encased within a housing to prevent pieces of the foam falling into the surgical area. However, this adds to the manufacturing expense. The teachings of the present invention recognize that incorporating inflatable bladders 104 around a perimeter of open end 110 may cause greater expense in manufacturing surgical drape 100; however, the applicants believe that surgical drape 100 may be manufactured in a cost-effective manner.

In the illustrated embodiment, four inflatable bladders 104 are shown; however, one or any suitable number of inflatable bladders 104 may be utilized. Inflatable bladders 104 are generally elongated air bladders having any suitable length that are formed from any material suitable to contain pressurized air therein. Although the teachings of the present invention recognize that medical personnel may not desire to use surgical drape 100 with inflatable bladders 104 because of the risk of puncturing them due to the sharp objects often employed in medical procedures, steps may be taken to mitigate this risk by, for example, using a thicker plastic to form inflatable bladders 104. In the illustrated embodiment, inflatable bladders 104 are housed within channel 112 around the perimeter of open end 110. However, in an embodiment where channel 112 does not exist, inflatable bladders 104 may be directly coupled to fluid collection pouch 102 around the perimeter of open end 110 in any suitable manner. In other embodiments, one or more inflatable bladders 104 may be disposed generally vertically down, or generally horizontally around, the wall of collection pouch 102 to add additional stiffness to the wall of collection pouch 102.

Pumps 106 are coupled to inflatable bladders 104 in any suitable manner and are operable to inflate inflatable bladders 104 in any suitable manner, such as the manner described in U.S. Pat. No. 5,144,708 (the '708 patent) issued to Pekar and assigned to Dielectrics Industries of Chicopee, Mass., which is incorporated herein by reference. Any suitable type of pump 106 is contemplated by the present invention, as well as other suitable types of inflating devices or methods. Various examples of pumps 106 are shown and described below in conjunction with FIGS. 2B through 2E. In the embodiment illustrated in FIG. 1, each pump 106 includes an open cell foam structure disposed between a pair of plastic sheets, with one of the plastic sheets having an aperture formed therein to allow ambient air to enter the open cell foam. A check valve (such as the one disclosed in the '708 patent) is coupled to one end of the pump to allow air within the open cell foam structure to enter into inflatable bladder 104. The check valve prevents air within inflatable bladder 104 from traveling into pump 106. Accordingly, in operation, a user places his or her finger or thumb over the aperture in one of the plastic sheets and depresses the open cell foam structure so that air is pushed through the check valve and into inflatable bladder 104. The user would then release the pressure exerted on the open cell foam structure and remove his or her finger from over the aperture so that ambient air may fill the open cell foam structure. The process above is then repeated until a desired pressure is obtained within inflatable bladder 104.

Although two pumps 106 are shown in FIG. 1, one pump 106 or any suitable number of pumps 106 may be utilized. In one embodiment, pump 106 is generally rectangular in shape; however, any suitably shaped pump may be utilized. Similarly to inflatable bladders 104, pumps 106 may either be housed within channel 112 or, in an embodiment where channel 112 does not exist, be coupled to a perimeter of open end 110 of fluid collection pouch 102 in any suitable manner. The present invention also contemplates pumps 106 being external to inflatable bladders 104 and/or channel 112, such as those shown and described below in conjunction with FIGS. 2C through 2E; however, it is desirable to house pumps 106 within channel 112 because this makes the packaging and shipping of surgical drape 100 easier. In addition, housing pumps 106 within channel 112 provides a more convenient way of inflating inflatable bladders 104 as well as eliminating any interference problems with a surgical procedure. Channel 112 may also protect pumps 106 from surgical and/or bodily fluids during surgery.

Patient drape 108 may be coupled to fluid collection pouch 102 in any suitable manner depending on what portion of a patient's body that patient drape 108 is to protect. Patient drape 108 may be any suitable shape and may be formed from any suitable material. As illustrated in FIG. 1, patient drape 108 shields the rest of the patient's body from the surgical area.

Surgical drape 100 will generally be packaged and shipped to a prospective user with inflatable bladders 104 in a deflated state, which is shown in FIG. 2A. Packaging and shipping surgical drape 100 with deflated inflatable bladders 104 is easier and less expensive than packaging and shipping previous surgical drapes that had foam material rims. Pumps 106 are utilized to inflate inflatable bladders 104. FIGS. 2B through 2E illustrate inflatable bladders 104 being inflated by various examples of pumps 106.

Referring to FIG. 2B, a user 200 simply uses his or her fingers and thumb to alternately squeeze and release pump 106 to suck in ambient air from outside pump 106 into pump 106 and through a check valve coupled to pump 106 and into inflatable bladders 104. This pumping continues until a desired stiffness of inflatable bladders 104 is obtained. Similarly, referring to FIG. 2C, user 200 may utilize a suitable squeeze bulb 210 having a suitable check valve to pump ambient air into inflatable bladders 104. Another type of pump 106 is illustrated in FIG. 2D. A hand pump 220 may be utilized by user 200 to pump air into inflatable bladders 104. Hand pump 220 may be any suitable hand pump, such as those used to inflate pool rafts, basketballs, and the like. As illustrated in FIG. 2E, a compressed air source 230 may be utilized by user 200 to inflate inflatable bladders 204. Any suitable compressed air source 230 is contemplated by the present invention. Other suitable example pumps 106 are chemical reaction type pumps, such as those with an acid and base, and a gas cartridge, such as a $CO_2$ cartridge. In other embodiments, no pump is utilized. For example, air from a human's lungs may be utilized to inflate inflatable bladders 104.

After the desired stiffness of inflatable bladders 104 is obtained, surgical drape 100 may then be placed in its desired position with respect to a patient with collection pouch 102 underneath the surgical site. Surgical and/or bodily fluids may then be collected by collection pouch 102 during the surgical procedure. After the surgical procedure is completed, fluids may be drained off and surgical drape 100 discarded. In other embodiments, fluids are drained off and surgical drape 100 is re-used for another surgical procedure.

FIG. 3 is a perspective view of another embodiment of a surgical drape 300 being utilized during a surgical procedure. In the illustrated embodiment, surgical drape 300 is coupled to a substrate 302. Substrate 302 may be any suitable substrate, such as a bed used in obstetrics, gynecology, or urology, or a surgical drape. Other intended uses for surgical drape 300 are contemplated by the present invention. Surgical drape 300 includes a fluid collection pouch 304, an inflatable bladder 306, a PUMP 308, and a flap 310.

Fluid collection pouch 304 is illustrated in FIG. 3 to be the general shape of a half of a cone; however, other suitable shapes may be utilized. Fluid collection pouch 304 is similar to fluid collection pouch 102 of FIG. 1 and functions in a similar manner. However, since fluid collection pouch 304 is contemplated for obstetrical, gynecological, or urological procedures, it differs from fluid collection pouch 102 in that it does not have apertures in its wall for a patient's limb. Otherwise, fluid may leak out of fluid collection pouch 304. Fluid collection pouch 304 includes an open end 314 that collects fluid from a surgical site and directs it into a fluid collection pouch 304. Fluid collection pouch 304 does include a drainage port 312 at a lower end thereof. Drainage port 312 is similar to drainage port 114 of FIG. 1 and functions in a similar manner.

A channel 316 surrounds approximately one-half of the perimeter of open end 314 and functions to house inflatable bladder 306. Channel 316 is similar to channel 112 of surgical drape 100 and may be formed in a similar manner. Channel 316 only surrounds approximately one-half of the perimeter of open end 314 because the other approximately one-half of the perimeter comprises flap 310. Flap 310, which may be any suitable length and width, includes an adhesive strip 318 that allows surgical drape 300 to be coupled to substrate 302 or other suitable medical platform. Flap 310 and adhesive strip 318 may both be formed from any suitable material.

Inflatable bladder 306 is similar to inflatable bladders 104 of FIG. 1 and is inflated by pump 308, which is similar to pumps 106 in FIG. 1. Any suitable number of inflatable bladders 306 may be utilized and any suitable number of pumps 308 may be utilized. Similar to surgical drape 100, surgical drape 300 will generally be packaged and shipped with inflatable bladder 306 being in a deflated state. Pump 308 is utilized by medical personnel to inflate inflatable bladder 306 to a desired stiffness. Drape 300 may be attached by flap 310 prior to or after inflation. Surgical drape 300 may then be attached to substrate 302 by flap 310 and adhesive strip 318. Surgical drape 300 is positioned in such a manner that open end 314 is underneath the desired surgical area. During the surgical procedure, surgical fluids and/or bodily fluids fall into fluid collection pouch 304 and collect near its bottom end. Drainage port 312 may then be used to drain the fluids off, or surgical drape 300 may be disposed of without draining the fluid. The advantages of using surgical drape 200 of FIG. 3 are similar to those proffered above in conjunction with surgical drape 100 of FIG. 1.

Although embodiments of the invention and some of their advantages are described in detail, a person skilled in the art could make various alterations, additions, and omissions without departing from the spirit and scope of the present invention as defined by the appended claims.

What is claimed is:

1. A method, comprising:
providing a fluid collection pouch having an open end and one or more inflatable bladders disposed within a channel around a perimeter of the open end, the one or more inflatable bladders extending around substantially all of the perimeter of the open end, the one or more bladders forming a rim around the perimeter of the open end of the fluid collection pouch, the one or more inflatable bladders pushing the rim of the portion of the perimeter of the fluid collection pouch that is not connected to the patient drape outwardly from the patient drape;
inflating the inflatable bladders;
coupling the fluid collection pouch to the patient drape configured to shield a portion of the patient's body; and
collecting fluids in the fluid collection pouch as a result of a treatment of a patient.

2. The method of claim 1, further comprising draining fluids from the fluid collection pouch.

3. A system used for collecting fluids during a medical procedure, comprising:

a patient drape configured to shield a portion of a patient's body during a medical procedure;

a fluid collection pouch coupled to the patient drape and configured for the collection of fluids during a treatment of a patient, the fluid collection pouch having an open end;

a channel surrounding substantially all of a perimeter of the open end;

an elongated inflatable bladder disposed within the channel, the elongated inflatable bladder extending around substantially all of the perimeter of the open end, and forming a rim around the perimeter of the open end of the fluid collection pouch, the elongated inflatable bladder pushing the rim of the portion of the perimeter of the fluid collection pouch that is not connected to the patient drape outwardly from the patient drape; and an inflating device for inflating the inflatable bladder.

4. The system of claim 3, further comprising an aperture formed in a wall of the fluid collection pouch, the aperture adapted to accept a limb of a patient.

5. The system of claim 3, further comprising opposed apertures formed in a wall of the fluid collection pouch, the apertures adapted to accept a limb of a patient.

6. The system of claim 3, further comprising a drainage port coupled to a wall of the fluid collection pouch for draining fluid from the fluid collection pouch.

7. The system of claim 3, wherein the inflating device is a carbon dioxide cartridge.

8. The system of claim 3, wherein the inflating device is a squeeze bulb.

9. The system of claim 3, wherein the inflating device is a hand pump.

10. The system of claim 3, wherein the inflating device is a compressed air source.

11. The system of claim 3, wherein the inflating device is a chemical reaction type pump.

12. The system of claim 3, wherein the inflating device is a pump.

13. A method, comprising:
providing a fluid collection pouch having an open end and one or more inflatable bladders disposed around substantially all of a perimeter of the open end, the one or more inflatable bladders forming a rim around the perimeter of the open end of the fluid collection pouch that is not connected to a patient drape, the one or more inflatable bladders pushing the rim of the portion of the perimeter of the fluid collection pouch outwardly from the patient drape;
inflating the inflatable bladders;
coupling the fluid collection pouch to the patient drape configured to shield a portion of the patient's body; and
collecting fluids in the fluid collection pouch as a result of a treatment of a patient.

14. The method of claim 13, further comprising positioning a limb of a patient through an aperture formed in a wall of the fluid collection pouch.

15. The method of claim 13, further comprising positioning a limb of a patient through opposing apertures formed in a wall of the fluid collection pouch.

16. The method of claim 13, further comprising draining fluids from the fluid collection pouch.

17. The method of claim 13, wherein inflating the inflatable bladders comprises using a carbon dioxide cartridge to inflate the inflatable bladders.

18. The method of claim 13, wherein inflating the inflatable bladders comprises using a squeeze bulb to inflate the inflatable bladders.

19. The method of claim 13, wherein inflating the inflatable bladders comprises using a hand pump to inflate the inflatable bladders.

20. The method of claim 13, wherein inflating the inflatable bladders comprises using a compressed air source to inflate the inflatable bladders.

21. The method of claim 13, wherein inflating the inflatable bladders comprises initiating a chemical reaction to inflate the inflatable bladders.

22. A system used for collecting fluids during a medical procedure, comprising:
a patient drape configured to shield a portion of a patient's body during a medical procedure;
a fluid collection pouch coupled to the patient drape and configured for the collection of fluids during a treatment of a patient, the fluid collection pouch having an open end;
an elongated inflatable bladder disposed around substantially all of a perimeter of the open end, the elongated inflatable bladder forming a rim around the perimeter of the open end of the fluid collection pouch, the elongated inflatable bladder pushing the rim of the portion of the perimeter of the fluid collection pouch that is not connected to the patient drape outwardly from the patient drape; and
an inflating device for inflating the inflatable bladder.

23. The system of claim 22, further comprising an aperture formed in a wall of the fluid collection pouch, the aperture adapted to accept a limb of a patient.

24. The system of claim 22, further comprising opposed apertures formed in a wall of the fluid collection pouch, the apertures adapted to accept a limb of a patient.

25. The system of claim 22, further comprising a drainage port coupled to a wall of the fluid collection pouch for draining fluid from the fluid collection pouch.

26. The system of claim 22, wherein the inflating device is a carbon dioxide cartridge.

27. The system of claim 22, wherein the inflating device is a squeeze bulb.

28. The system of claim 22, wherein the inflating device is a hand pump.

29. The system of claim 22, wherein the inflating device is a compressed air source.

30. The system of claim 22, wherein the inflating device is a chemical reaction type pump.

31. The system of claim 22, wherein the inflating device is a pump.

* * * * *